US009742432B2

(12) United States Patent
Kmiecik et al.

(10) Patent No.: US 9,742,432 B2
(45) Date of Patent: Aug. 22, 2017

(54) ACCELEROMETER DATA COMPRESSION

(75) Inventors: Marcin Michal Kmiecik, Lódz (PL);
Nelson Miguel Da Cruz Gonçalves,
Lódz (PL); Ying-Lin Lai, Taipei (TW)

(73) Assignees: TomTom International B.V.,
Amsterdam (NL); **TomTom Polska Sp.
z o.o**, Warszawa (PL)

(*) Notice: Subject to any disclaimer, the term of this patent is extended or adjusted under 35 U.S.C. 154(b) by 622 days.

(21) Appl. No.: 13/977,880

(22) PCT Filed: Dec. 31, 2010

(86) PCT No.: PCT/EP2010/070966
§ 371 (c)(1),
(2), (4) Date: Sep. 26, 2013

(87) PCT Pub. No.: WO2012/089278
PCT Pub. Date: Jul. 5, 2012

(65) Prior Publication Data
US 2014/0046990 A1 Feb. 13, 2014

(51) Int. Cl.
*A61B 5/00* (2006.01)
*H03M 7/30* (2006.01)
(Continued)

(52) U.S. Cl.
CPC ............. *H03M 7/30* (2013.01); *A61B 5/1112* (2013.01); *A61B 5/7232* (2013.01);
(Continued)

(58) Field of Classification Search
CPC .............................. A61B 5/1112; A61B 5/7232
(Continued)

(56) References Cited

U.S. PATENT DOCUMENTS 6,539,336 B1 * 3/2003 Vock .................... A42B 3/0433
702/178
7,764,641 B2 * 7/2010 Pelton .................... H04W 4/001
370/328

(Continued)

OTHER PUBLICATIONS

Ning Xu: "Implementation of Data Compression and FFT on TinyOS", Jan. 1, 2005, XP55007992, Retrieved from the Internet: URL:http://en1.usc.edu/-om p/1zfft.pdf [retrieved on Sep. 23, 2011].

(Continued)

*Primary Examiner* — Bryan Bui

(57) ABSTRACT

A method of compressing data output from one or more accelerometers configured to be transported, carried or worn by a user is provided. Acceleration values indicative of the movement of the user are measured at a first frequency and values representative of the measured acceleration values are generated at a second frequency, which is lower than the first frequency. The step of generating comprises: defining a plurality of time windows, each time window containing a plurality of measured acceleration values; and applying a transformation to the measured acceleration values within each time window to generate a plurality of transformed values. For each time window, storing at least one of said plurality of transformed values and/or one or more parameters associated therewith.

20 Claims, 13 Drawing Sheets

(51) Int. Cl.
*A61B 5/11* (2006.01)
*G01C 22/00* (2006.01)

(52) U.S. Cl.
CPC ............ *G01C 22/006* (2013.01); *A61B 5/681* (2013.01); *A61B 2503/10* (2013.01); *A61B 2560/0475* (2013.01); *A61B 2562/0219* (2013.01); *A61B 2562/227* (2013.01)

(58) Field of Classification Search
USPC .......................................................... 702/141
See application file for complete search history.

(56) References Cited

U.S. PATENT DOCUMENTS

| 2007/0111753 | A1 | 5/2007 | Vock et al. | |
|---|---|---|---|---|
| 2008/0214360 | A1* | 9/2008 | Stirling | A61B 5/1038 482/9 |
| 2009/0132197 | A1* | 5/2009 | Rubin | H04M 1/72563 702/141 |

OTHER PUBLICATIONS

Shengpu Liu et al: "Efficient Data Compression in Wireless Sensor Networks for Civil Infrastructure Health Monitoring" 2006 3rd Annual IEEE Communications Society Conference on Sensor and Ad Hoc Communications and Networks—Sep. 25-28, 2006—Reston. VA. USA. IEEE, Piscataway, NJ, USA, Jan. 1, 2006. pp. 823-829. XP031012272. ISBN: 978-1-4244-0626-51V. * IV. System Design; A. Simulation System Structure; B. Compression Process *.

"Digital Triaxial Vibration Sensor with FFT Analysis and Storage". Oct. 31, 2010. XP55007993. Retrieved from the Internet: URL:http://www.analog.com/static/importedffies/data sheets/ADISI6227.pdf [retrieved-on Sep. 23, 2011].

International Search Report issued Oct. 5, 2011 for International Application No. PCT/EP2010/070966.

* cited by examiner

FILE HEADER

| Field | Meaning | Size |
|---|---|---|
| File version | Version of the acc file | 2 bytes |
| Header size | For backward/forward compatibility | 2 bytes |
| Block header size | For backward/forward compatibility | 2 bytes |
| Device firmware | Mapping of firmware version number of device | 2 bytes |
| Acc software | Mapping of firmware version number of acc device | 2 bytes |

FIG. 6a

DATA BLOCK

| Field | Meaning | Size |
|---|---|---|
| DC value | Value of zero amplitude | 1 byte |
| Max index | Frequency (index) of maximal amplitude (excl DC) | 1 byte |
| Max value | Value of maximum amplitude (excl. DC) | 1 byte |
| Energy excl. DC | Sum of all amplitudes in the frequency excluding zero frequency (DC) | 1 byte |

FIG. 6b

ACCELEROMETER DATA COMPRESSION

CROSS-REFERENCES TO RELATED APPLICATIONS

This application is the National Stage of International Application No. PCT/EP2010/070966 filed Dec. 31, 2010 and designating the United States. The entire content of this application is incorporated herein by reference.

FIELD OF INVENTION

This invention relates to a method of compressing data, such as from sensors for monitoring the dynamical movements of a mobile device and/or a user of the device, for storage of said data on the mobile device. Illustrative embodiments of the invention relate to portable training devices, e.g. devices that can be worn, carried or transported by runners, cyclists, etc during a journey or workout.

BACKGROUND OF THE INVENTION

Many people who exercise, such as runners, cyclists or the like, often desire the ability to monitor their workouts for performance and motivation reasons. To meet this need, many personal training devices are available on the market for monitoring and in some cases tracking a run, ride or workout.

One example of personal training devices are step counters (or pedometers), foot-pad sensors (e.g. accelerometers) and tachometers. These devices can monitor and track the distance travelled by a user, e.g. a runner, by counting the number of steps made by runner.

In recent years, the use of GNSS (Global Navigation Satellite Systems) receivers, such as GPS, has started to be used in personal training devices. For example, sports watches that include GPS antennas have started to be used by joggers, runners, cyclists and other athletes and outdoor enthusiast as a means to obtained real-time data of their speed, distance travelled, etc. Unlike the step sensors mentioned above, these GPS devices provide the user with the ability to track and record the route they have travelled, and to subsequently "map" this route for later analysis. For example, the GPS data stored on such devices can be transferred to a computer or website by a user after they have completed their activity so that the route can be displayed on a digital map.

As will be understood by those skilled in the art, the position and speed data obtained from GPS receivers will typically be effected by slowly time-varying errors. Such errors can be reduced to a large extent in vehicle navigation systems, such as conventional portable navigation systems (PNDs), using various filtering techniques such as Kalman filtering and map matching. The different, and generally more complex, dynamical behaviour of pedestrians and other outdoor enthusiasts, however, means that conventional filtering techniques cannot be used, or at least are significantly less effective. Furthermore, many runners, cyclists, etc will carry out their exercise areas where satellite visibility might be impaired, e.g. dense urban environments having numerous tall buildings. Accordingly, when the GPS traces obtained from conventional personal training devices are displayed on a digital map, the route shown may contain numerous inaccuracies, both small and large, when compared to the route actually travelled by the user.

It would therefore be desirable to provide a mobile device that can record data associated with the route travelled by a user in a manner that allows a more accurate route to be displayed on a digital map. Since the data storage capability of such mobile devices is generally rather limited, it would also be desirable to record data relating to the route in an efficient, or compressed, manner.

SUMMARY OF THE INVENTION

According to a first aspect of the present invention, there is provided a method of compressing data output from an acceleration measurement means configured to be transported, carried or worn by a user, comprising the steps of:
measuring acceleration values indicative of the movement of the user at a first frequency;
generating values representative of the measured acceleration values at a second frequency, which is lower than the first frequency, said step of generating comprising:
defining a plurality of time windows, each time window containing a plurality of measured acceleration values; and
applying a transformation to the measured acceleration values within each time window to generate a plurality of transformed values; and
for each time window, storing at least one of said plurality of transformed values and/or one or more parameters associated therewith.

Similarly, according to a second aspect of the present invention, there is provided a system configured to be transported, carried or worn by a user, comprising:
means for measuring acceleration values indicative of the movement of the user and/or device at a first frequency;
means for generating values representative of the measured acceleration values at a second frequency, which is lower than the first frequency, said means being configured to:
define a plurality of time windows, each time window containing a plurality of measured acceleration values; and
apply a transformation to the measured acceleration values within each time window to generate a plurality of transformed values; and
data storage means for storing, for each time window, at least one of said plurality of transformed values and/or one or more parameters associated therewith.

In the present invention, data output from an acceleration measurement means configured to be transported, carried or worn by a user is compressed to facilitate storage, such that the stored data can be used in the future.

As will be appreciated, a system is provided that is arranged to be transported, carried or worn by a user. The system can comprise a single device (containing one or more sensors) or it may comprise a plurality of devices and sensors that are worn or carried about a person's body. In embodiments wherein the sensors are external from a main body, e.g. a mobile device, then preferably the mobile device comprises means for receiving data from the sensors.

In a preferred embodiment, however, the acceleration measurement means is provided in a mobile or portable device that is carried by a user as he or she travels from one locate to another. The mobile device can be arranged so as to be carried by the user, such as being attached to the user's arm or wrist, or simply by being placed in a pocket or other suitable receptacle (e.g. a specially designed holder or case). In other embodiments, the mobile device can be arranged so as to be transported carried by a user, e.g. a bicycle, canoe, kayak or other similar vehicle. The mobile device could also be attached to an object being pushed or pulled by a user, such as a child-carrying buggy. Such mobile devices are commonly referred to as portable personal training devices.

It should be appreciated that such mobile devices, i.e. portable personal training devices, preferably do not include navigation functionality as found in vehicle PNDs. For example, portable personal training devices typically, and in preferred embodiments of the present invention, do not include map data stored within a memory of the device or processing means that can use the map data to determine a route between a first location (or "origin") and a second location (or "destination") and provide suitable navigation (or guidance) instructions.

It has been recognised that by measuring and storing data associated with the accelerations experienced by the user and/or the device during a run, ride or the like, i.e. monitoring the dynamical movements of the user and/or device, then this stored information can be used, together with data indicating the location of the user and/or device, to provide a higher quality representation of the route travelled by the user when display on a digital map. For example, the measured acceleration can be used as an input (possibly one of a number of inputs) to an algorithm for "smoothing" an obtained GPS trace. Due to the restricted memory capacity available on such mobile devices, it is typically not possible to store all the data output from the acceleration measurement means, e.g. one or more accelerometers (as described in more detail below), but it has been recognised in the present invention that preferably only a limited number of data values associated with and/or parameters derived from the measured acceleration values need to be stored. More specifically, in the present invention, a plurality of (preferably equal-sized) time windows are defined, each encompassing a plurality of measured acceleration values, and the values within each time window are transformed to generate a plurality of transformed values. As will be discussed in more detail below, the transformation preferably comprises a transformation from the time domain to the frequency domain, such as a Fourier transformation. One or more of the transformed values and/or parameters derived from the transformed values are stored for each of the defined time windows on a data storage means of the device, and it is these stored values (which are effectively a lossy compressed form of the measured acceleration values) that are used to help enhance the quality of the displayed route (as travelled by the user).

The mobile device of the present invention comprises means for measuring an acceleration value indicative of the movement of the user and/or device. In other words, the means is arranged to detect changes in acceleration of the mobile device, and thus directly (when the device is worn or carried by the user) or indirectly (when the device is transported by the user) changes in the movement and/or direction of the user.

The means can comprise any suitable and desired sensors, e.g. that can detect the movement of the device. For example, in a preferred embodiment, the acceleration measurement means comprises one or more accelerometers for determining the magnitude and direction of the acceleration, e.g. in at east two, and preferably three, axes. The accelerometers can be single-axis accelerometers or multi-axis accelerometers. For example, in a particularly preferred embodiment, the mobile device comprises a three-axis accelerometer. Any suitable type of accelerometer can be used in the present invention as desired, such as piezoelectric accelerometers and micro-machined (or MEMS) accelerometers.

The mobile device may further have access to data from one or more external motion sensors (e.g. for detecting accelerations experienced by the user). For example, the mobile device may comprise communication means, at least, for receiving data from a foot pad sensor (worn by the user). The foot pad sensor, as known in the art, may comprise a piezoelectric sensor (accelerometer), e.g. that is positioned in the user's shoe (e.g. in the sole thereof) and detects each time the shoe strikes the ground.

Indeed, it is contemplated, albeit in less preferred embodiments, that the mobile device itself may not comprise means for measuring an acceleration value indicative of the movement of the user. In such embodiments, the user can carry or wear the required acceleration sensors, e.g. as a footpad sensor in their shoe, or strapped to their arm, wrist, etc, and the mobile device comprises means for receiving data from the external sensor or sensors, such as a wireless receiver.

The acceleration sensors of the present invention can determine an acceleration of the user and/or device at any suitable frequency (or rate) as desired. However, in a preferred embodiment, the sensors are arranged to determine an acceleration of the user and/or device at a rate of 1 Hz or greater, preferably 2 Hz or greater, such as up to rate of 20 Hz, and most preferably at either 5 Hz or 10 Hz.

Measuring the dynamical movements of the user at such rates allows the movement of the user to be accurately established. Research into human dynamics has established that a typical human walking frequency is around 1 Hz and a typical human running frequency is around 3 Hz. Accordingly, by measuring an acceleration of the user at a rate above, but in the vicinity of, about 3 Hz, then the required dynamical movements of the user will be recorded without the level of noise being too high (i.e. without the signal to noise ratio (S/N) being at an unacceptable level).

The acceleration values received from the acceleration measurement means are preferably stored, at least temporarily, on the mobile device. For example, in a preferred embodiment, the mobile device comprises a data buffer into which the acceleration values measured over a predetermined time period are stored.

Preferably, the data buffer is a FIFO memory unit, such that data values are ordered within the buffer based on the time of measurement. As known in the art, once the buffer is "full", for each new acceleration value that enters the buffer, the oldest stored acceleration value exits the buffer and is discarded (or in other embodiments is made available for use in other processes being performed by the mobile device, such as in speed and distance calculations). The use of such a buffer, and particularly a FIFO memory unit, allows the values to be easily sampled and analysed as will be discussed in more detail below.

In those embodiments in which acceleration is measured along two or more perpendicular axes (e.g. in x, y and z directions), two or more data buffers can be provided as appropriate to temporarily store the acceleration values associated with each axis for a predetermined time period. Alternatively, and in a preferred embodiment, the perpendicular acceleration components are used to determine the absolute acceleration value at a given time, and thus in such embodiments only a single data buffer is required for temporarily storing the determined absolute acceleration values for a given period of time.

Therefore, in a preferred embodiment, the present invention further comprises means for and a step of determining an absolute acceleration value indicative of the movement of the user and/or device.

The step of determining an absolute acceleration value can occur at any suitable and desired rate as appropriate. For example, the determining step preferably occurs at the aforementioned first rate. However, in other embodiments, and in particular in those embodiments wherein the measured acceleration values for each separate axis are buffered, the determining step can occur at a rate less than the first rate.

In the present invention, the measured acceleration values, and preferably the determined absolute acceleration values, are then sampled and transformed to allow the data to be more easily compressed. Specifically, a plurality of time windows are defined, and the acceleration values within each time window are transformed to generate a plurality of transformed values.

The time windows can be of any suitable length as desired, and, for example, will often depend on the measurement rate of the accelerations sensors. For example, the length of the time windows can be chosen such that each window contains a particular number of acceleration values. The number of acceleration values is preferably between 10 to 100, and most preferably 50. The length of the time windows can alternatively be chosen such that each window is of a predefined length. For example, the length of each time window can be between 1 and 10 seconds, and most preferably 5 seconds.

It will be appreciated, therefore, that if the measurement rate of the acceleration sensor(s) changes (e.g. if the dynamical movement of the user requires the sensors to obtain measurements at a quicker or faster rate, or if the user purposively selects a different measurement rate), then the length of the time windows may change accordingly so as to maintain the number of values within each window. Alternatively, the length of the time windows may be kept the same, resulting in the number of values within each time window increasing or decreasing as appropriate.

Each time window may be defined so as to be next to one another, e.g. i.e. so that each time window encompasses a completely different set of acceleration values. In other words, one time window ends before the following window starts. Adjacent windows may be touching in such embodiments, or there may be a gap between adjacent time windows.

In a preferred embodiment of the present invention, however, the time windows are defined so as to be interleaving, i.e. at least a portion of one time window overlaps a portion of an adjacent time window, such that adjacent windows contain at least some, although not all, of the same acceleration values. By overlapping the time windows, the effect of performing a transformation, such as a Fourier transformation, on a short period of data can be mitigated. Thus, the values generated from transforming the measured acceleration will be more representative of the actual measured acceleration than would have been the case if no interleaving had been implemented.

The degree of overlap between adjacent time windows is such so as to "sample" the measured acceleration values at a rate that is less than the measurement rate (also referred to above as the "first frequency"), i.e. the rate at which the sensors are arranged to determine an acceleration of the user and/or device. In other words, the time between the start of one time window and the adjacent time window defines a sampling period (the inverse of which is the sampling rate, also referred to above as the "second frequency"). The sampling rate can be between 0.1 and 2 Hz, and preferably 0.5 Hz or 1 Hz.

For example, in a particularly preferred embodiment in which the sensors are arranged to determine an acceleration of the user and/or device at a rate of 10 Hz, each time window is offset from each other by 1 second equating to a sampling rate of 1 Hz.

As mentioned above, the acceleration values within each time window, e.g. the absolute acceleration experienced by the user and/or device at a plurality of different times, are subjected to a transformation to generate a plurality of transformed values. The transformation can comprise any suitable transformation, e.g. as known in the art, such as a Fourier-based transformation, Fourier-related transformation (such as a discrete cosine transformation (DCT)), wavelet-based transformation or the like. In all these transformations, it will be appreciated that the original data set is transformed into a plurality of coefficients (depending on the exact transformation used), which are more suitable for being compressed than the original data.

For example, in a particularly preferred embodiment, a fast Fourier transform (FFT) is applied to each time window, thereby creating one or more, typically a plurality of, frequency coefficients associated with each time window. In other words, the data within each time window is transformed to generate a corresponding frequency spectrum.

Therefore, according to a preferred embodiment of the present invention, the method comprises applying a transformation to the acceleration values within each time window to generate a frequency spectrum, and storing one or more parameters associated with the frequency spectrum.

As will be appreciated by those skilled in the art, these aspect of the invention can, and preferably do, include one or more or all of the preferred and optional features of the invention described herein, as appropriate.

As discussed above, and as will be appreciated by those skilled in the art, the transformed values generated in respect of each time window preferably comprise a plurality of indexed coefficients (e.g. frequency coefficients in the case of a Fourier-based transformation, each coefficient being associated with a particular frequency index).

It is contemplated, in at least some embodiments, that all the indexed coefficients generated for each time window are stored for future use, e.g. the amplitude of each coefficient is stored together with the associated index. The "compression" of the data in these embodiments is from the sampling of the measured data at a rate less than the measured rate, rather than from the transformation itself.

In a preferred embodiment of the present invention, however, only some (e.g. one or more) of the indexed coefficients may be stored for future use. In these embodiments, it will be appreciated that the invention comprises two stages of "compression": firstly the reduction in data by sampling the measured data at a rate less than the measured rate; and secondly by storing only a portion of the transformed data. For example, only those coefficients that have an amplitude above a predetermined threshold value may be stored. This may result, for example, in one or more or all of the following being stored: the zero index amplitude; the largest amplitude (and associated index); the second largest amplitude (and associated index); or so on until the amplitude drops below the predetermined threshold.

In other embodiments of the present invention, one or more parameters derived from the indexed coefficients may, additionally or alternatively, be calculated and stored. For example, the sum of the all of the amplitudes (preferably excluding the zero index amplitude) can be stored.

In a particularly preferred embodiment of the present invention, for each time window at least one, and preferably some or all, of the following information is stored: the zero index amplitude; the largest amplitude (excluding the zero index amplitude); the index associated with the largest amplitude; and the sum of all the amplitudes (excluding the zero index amplitude). It has been recognised that these four pieces of data for each time window provide sufficient information to indicate the dynamical movement being experienced by the user and/or device over a period of time, e.g. such that the route travelled by the user can be enhanced when it is shown on a digital map.

The at least one transformed value and/or one or more parameters associated therewith obtained from each time window can be stored in the data storage means in any suitable and desired manner. Preferably, however, the data is stored in a particular file format comprising a file header and a plurality of data blocks, wherein each data block contains one of the pieces of data to be stored. For example, using the above example, the file would have four data blocks. The first data block would contain the zero index amplitude. The second data block would contain the largest amplitude. The third data block would contain the index associated with the largest amplitude. Finally, the fourth data block would contain the sum of all the amplitudes.

As will be appreciated the steps of sampling and transforming the measured acceleration values are performed using one or processing resources, which are in communication with the various sensors of the mobile device and the data storage means.

The data storage means of the mobile device can be any suitable memory unit as desired, e.g. volatile or non-volatile. However, in a preferred embodiment, the data storage means comprises a non-volatile semiconductor memory, such as electrically erasable programmable read-only memory (EEPROM) and flash EEPROM. The data storage means can be integral with the mobile device. Alternatively, the data storage means can be removable.

As discussed above, the acceleration data that is obtained and stored on the mobile device of the present invention, is preferably used to adjust or modify the record of the route taken by a user during a journey when it is to be displayed on a digital map. Accordingly, it will be appreciated, that the mobile device of the present invention preferably further comprises means for determining the location of the device (e.g. to track the journey taken by the user from a first location to a second location).

The location determining means can comprise any suitable device as desired. For example, latitude and longitude coordinates can be determined using devices that can access and receive information from WiFi access points or cellular communication networks. Preferably, however, the location determining means comprises a global navigation satellite systems (GNSS) receiver, such as a GPS receiver, for receiving satellite signals indicating the position of the user at a particular point in time, and which receives updated position information at regular intervals.

Preferably, the GNSS receiver comprises a patch antenna or helical antenna, but it may comprise any other type of antenna capable of receiving satellite signals. The antenna is preferably at least partially encased or contained within a housing of the mobile device.

In a preferred embodiment, new location information, i.e. the geographic location of the device, is received at a rate of 0.5 Hz or greater, preferably at a rate of 1 Hz or greater, such as up to a rate of 20 Hz. In a particularly preferred embodiment, the new location information is received at a rate of 1 Hz. As known in the art, the location information comprises at least longitude and latitude, and can preferably also include elevation.

In a preferred embodiment, an acceleration of the user and/or device (as obtained from the acceleration measuring means described above) is determined at the same rate, or a faster rate, as the current location of the device is determined by the location determining means. Preferably, the location determining means and the acceleration measurement means are arranged to operate in a synchronous manner.

Preferably, at least some of the location information obtained from the GNSS receiver is stored on the (or a further) data storage means of the mobile device, e.g. for subsequent use in displaying the route travelled by the user on a digital map.

Although in preferred embodiments such location determining means will be provided in the same device as the acceleration sensors and other processing resources of the present invention, it is contemplated that the user may, for example, carry, wear or transport two separate devices, one for determining and tracking his or her location and the other for performing the steps of the present invention. The two devices may be linked such that the location determining means and acceleration sensors can obtain data in a synchronous manner, e.g. by a common time signal that can indicate at least the start and end of a journey.

It is believed that a mobile device, such as a personal portable training device, that is arranged to obtain and store data from at least a location determining means and an acceleration measurement means, e.g. for subsequent use in displaying a route on a digital map may be new and advantageous in its own right.

Thus, according to a third aspect of the present invention, there is provided a method comprising:

determining the location of a mobile device configured to be transported, carried or worn by a user at a plurality of times during a journey from a first location to a second location using location determining means;

measuring an acceleration value indicative of the movement of the user and/or device at a plurality of times during the journey using acceleration measurement means; and storing data received from and/or derived from the location determining means and the acceleration measurement means.

According to a fourth aspect of the present invention, there is provided a mobile device configured to be transported, carried or worn by a user, comprising:

means for determining the location of the device at a plurality of times during a journey from a first location to a second location;

means for receiving or measuring an acceleration value indicative of the movement of the user and/or device at a plurality of times during the journey; and data storage means for storing data received from and/or derived from the location determining means and a or the acceleration measurement means.

As will be appreciated by those skilled in the art, these aspects of the invention can, and preferably do, include one or more or all of the preferred and optional features of the invention described herein, as appropriate.

Thus, for example, the location determining means preferably comprises a GNSS receiver. Similarly, the acceleration measurement means preferably comprises one or more accelerometers, such as a three-axis accelerometer.

The mobile device may also have means for receiving data from one or more external motion sensors, such as a foot pad sensor (or accelerometer), and at least some of the data received from such sensors may also be stored, together with location and acceleration information, e.g. for use when the displaying the route travelled by the user on a digital map.

The data stored on the data storage means of the mobile device is preferably transferred to a central server, e.g. whereupon it is used to determine the route travelled by the user during the journey with respect to a digital map. The user can access this central server using, for example, the Internet, to retrieve the route and/or to display the route. The data on the mobile device can be transferred to the central server using any suitable and desired means. For example, the mobile device could be provided with wireless communication means to allow data stored on the data storage means to be transferred over the air, for example, to a computer or other device that has access to the Internet. Alternatively, and in a preferred embodiment, the mobile device comprises a data connector, such as a USB connector, that is connected to at least the data storage means. Data on the data storage means can therefore be transferred to a computer or other suitable device by inserting the connector into a suitable port.

As discussed above, the mobile device of the present invention preferably comprises a portable personal training device.

In a particularly preferred embodiment, the mobile device comprises a housing containing at least a portion, and preferably all, of the acceleration measurement means. Preferably, at least a portion, and preferably all, of the location determining means are also contained within the housing.

As discussed above, the mobile device can be configured so as to be carried or transported by a user. In a preferred embodiment, however, the housing of the mobile device comprises a strap for securing the housing to a user. The strap, for example, can be arranged to secure the housing to the user's wrist in the manner of a watch. In other words, the mobile device is preferably a sports watch.

In those embodiments in which the mobile device is a sports watch, the data connector is preferably provided at one end of the strap of the watch. The sports watch preferably comprises a protective cover that can be selectively opened or closed by the user. When in the "closed" position, the protective cover is positioned over the data connector, and preferably held in place by suitable releasable locking means, thereby protecting the data connector from damage when the watch is in use. When in the "open" position, the data connector is exposed and can be inserted into a complementary port of a computer or other suitable device.

The mobile device preferably comprises a display for providing information to the user, such as information as obtained or derived from the location determining means, e.g. distance travelled, current speed, average speed, elevation, etc. The display screen can include any type of display screen, such as an LCD display, e.g. that can display both text and graphical information.

The mobile device preferably comprises one or more input means to allow the user to select one or more functions of the device and/or to input information to the device, such as to display particular information on the display. The input means can comprise one or more buttons, switches or the like attached to the housing, a touch panel and/or any other suitable device. For example, the housing could be arranged to be touch sensitive such that the user can input information, request a change in the information being displayed, etc by touching appropriate portions of the housing. The input means and the display could be integrated into an integrated input and display device, including a touchpad or touch-screen so that a user need only touch a portion of the display to select one of a plurality of display choices or to activate a virtual button or buttons. The input means may additionally or alternatively comprise a microphone and software for receiving input voice commands.

The mobile device may include an audible output device, such as a loudspeaker, for providing audible information, such as instructions, alerts, etc to a user. For example, the output device can provide an indication when a target distance has been travelled and/or when a target speed has been achieved.

As will be appreciated, the mobile device will comprise a power source, e.g. for providing power to the various components and sensors of the device. The power source can take any suitable form, although in a preferred embodiment, the power source comprises a rechargeable battery, e.g. that can be recharged when the aforementioned data connector is inserted into a port on a computer or other suitable device. In other words, the data connector preferably comprises a power and data connector.

As will be appreciated by those skilled in the art, all of the aspects and embodiments of the invention described herein can and preferably do include any one or more of the preferred and optional features of the invention described herein, as appropriate.

The methods in accordance with the present invention may be implemented at least partially using software, e.g. computer programs. The present invention thus also extends to a computer program comprising computer readable instructions executable to perform a method according to any of the aspects or embodiments of the invention.

The invention thus also extends to a computer software carrier comprising software which when used to operate a system or apparatus comprising data processing means causes, in conjunction with said data processing means, said apparatus or system to carry out the steps of the methods of the present invention. Such a computer software carrier could be a non-transitory physical storage medium, such as a ROM chip, CD ROM or disk, or could be a signal, such as an electronic signal over wires, an optical signal or a radio signal such as to a satellite or the like.

Where not explicitly stated, it will be appreciated that the invention in any of its aspects may include any or all of the features described in respect of other aspects or embodiments of the invention to the extent that they are not mutually exclusive. In particular, while various embodiments of operations have been described which may be performed in the method and by systems or apparatus, it will be appreciated that any one or more or all of these operations may be performed in the method and by the system or apparatus, in any combination, as desired, and as appropriate.

Advantages of these embodiments are set out hereafter, and further details and features of each of these embodiments are defined in the accompanying dependent claims and elsewhere in the following detailed description.

BRIEF DESCRIPTION OF THE DRAWINGS

Various aspects of the teachings of the present invention, and arrangements embodying those teachings, will hereafter be described by way of illustrative example with reference to the accompanying drawings, in which:

FIG. 5b illustrates the output of the FFT of FIG. 5a;

FIG. 6a illustrates details of the file header of the file format of the invention;

FIG. 6b illustrates details of the data block of the file format of the invention;

FIG. 9 shows an embodiment of the device of FIG. 8, wherein the device is in the form of a sports watch, while FIG. 9a shows a USB connector in the device of FIG. 9;

Like reference numerals are used for the like features throughout the drawings.

DETAILED DESCRIPTION OF THE PREFERRED EMBODIMENTS

Preferred embodiments of the present invention will now be described with particular reference to a portable personal training device, such as a sports watch, having access to Global Positioning System (GPS) data. Sports watches after the type described are often worn by athletes to help them during their runs or workouts, e.g. by monitoring the speed and distance of the user and providing this information to the user. It will be appreciated, however, that the device could be arranged to be carried by a user or connected or "docked" in a known manner to a vehicle such as a bicycle, kayak, or the like.

Figure 1:
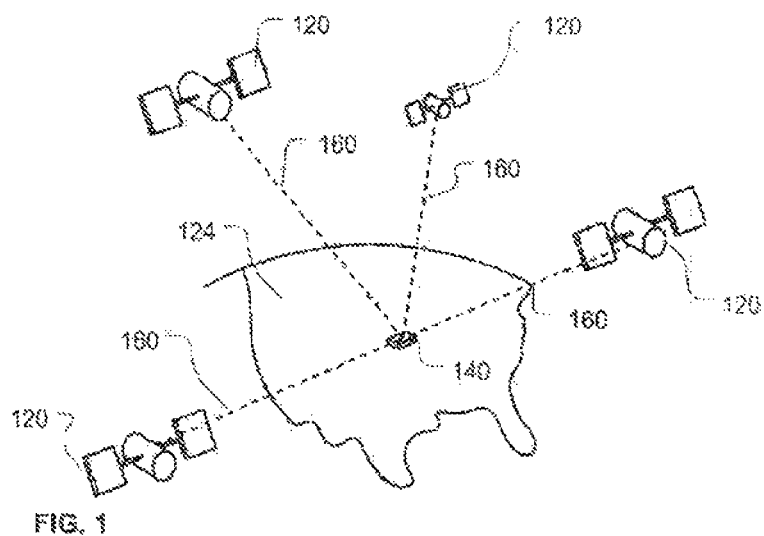
FIG. 1 is a schematic illustration of a Global Positioning System (GPS)

FIG. 1 illustrates an example view of Global Positioning System (GPS), usable by such devices. Such systems are known and are used for a variety of purposes. In general, GPS is a satellite-radio based navigation system capable of determining continuous position, velocity, time, and in some instances direction information for an unlimited number of users. Formerly known as NAVSTAR, the GPS incorporates a plurality of satellites which orbit the earth in extremely precise orbits. Based on these precise orbits, GPS satellites can relay their location to any number of receiving units.

The GPS system is implemented when a device, specially equipped to receive GPS data, begins scanning radio frequencies for GPS satellite signals. Upon receiving a radio signal from a GPS satellite, the device determines the precise location of that satellite via one of a plurality of different conventional methods. The device will continue scanning, in most instances, for signals until it has acquired at least three different satellite signals (noting that position is not normally, but can be determined, with only two signals using other triangulation techniques). Implementing geometric triangulation, the receiver utilizes the three known positions to determine its own two-dimensional position relative to the satellites. This can be done in a known manner. Additionally, acquiring a fourth satellite signal will allow the receiving device to calculate its three dimensional position by the same geometrical calculation in a known manner. The position and velocity data can be updated in real time on a continuous basis by an unlimited number of users.

As shown in FIG. 1, the GPS system is denoted generally by reference numeral 100. A plurality of satellites 120 are in orbit about the earth 124. The orbit of each satellite 120 is not necessarily synchronous with the orbits of other satellites 120 and, in fact, is likely asynchronous. A GPS receiver 140 is shown receiving spread spectrum GPS satellite signals 160 from the various satellites 120.

The spread spectrum signals 160, continuously transmitted from each satellite 120, utilize a highly accurate frequency standard accomplished with an extremely accurate atomic clock. Each satellite 120, as part of its data signal transmission 160, transmits a data stream indicative of that particular satellite 120. It is appreciated by those skilled in the relevant art that the GPS receiver device 140 generally acquires spread spectrum GPS satellite signals 160 from at least three satellites 120 for the GPS receiver device 140 to calculate its two-dimensional position by triangulation. Acquisition of an additional signal, resulting in signals 160 from a total of four satellites 120, permits the GPS receiver device 140 to calculate its three-dimensional position in a known manner.

Figure 8:
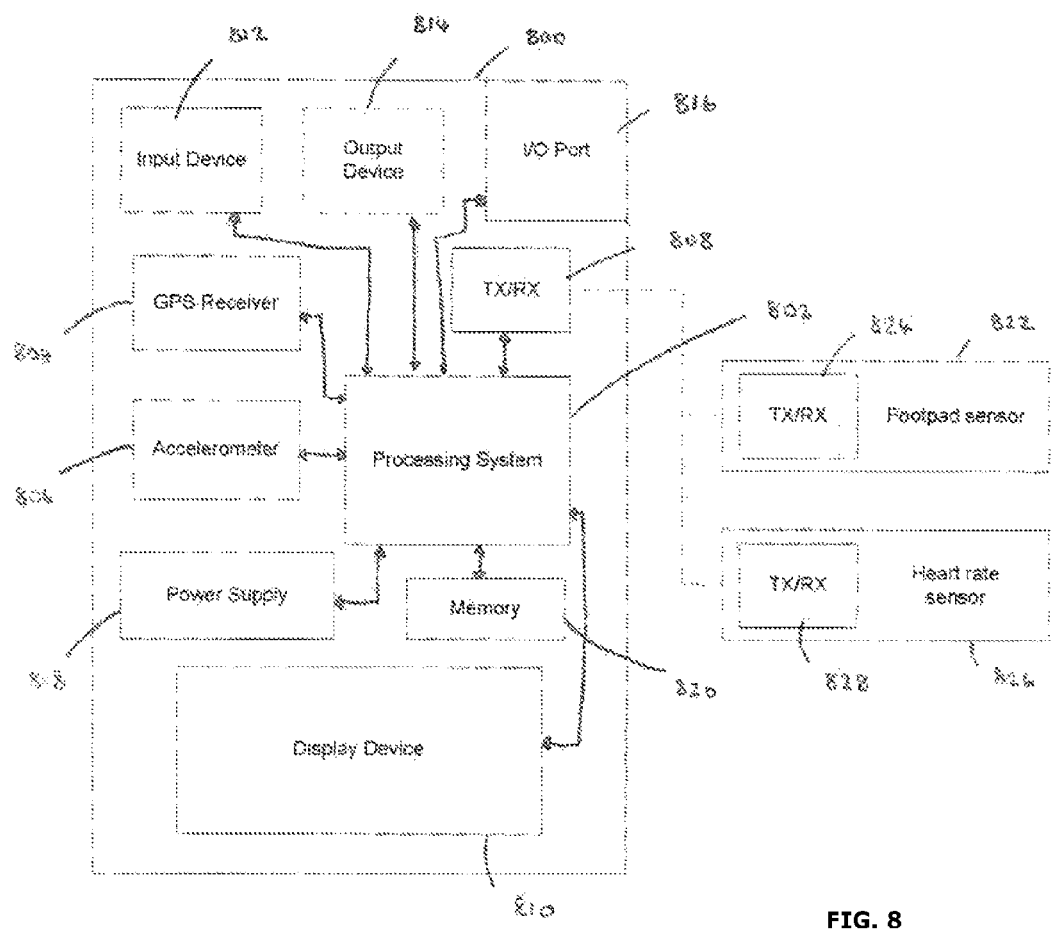
FIG. 8 is a schematic illustration of electronic components arranged to provide a portable personal training device.

FIG. 8 is an illustrative representation of electronic components of a personal portable training device 800 according to a preferred embodiment of the present invention, in block component format. It should be noted that the block diagram of the device 800 is not inclusive of all components of the navigation device, but is only representative of many example components.

Figure 9:
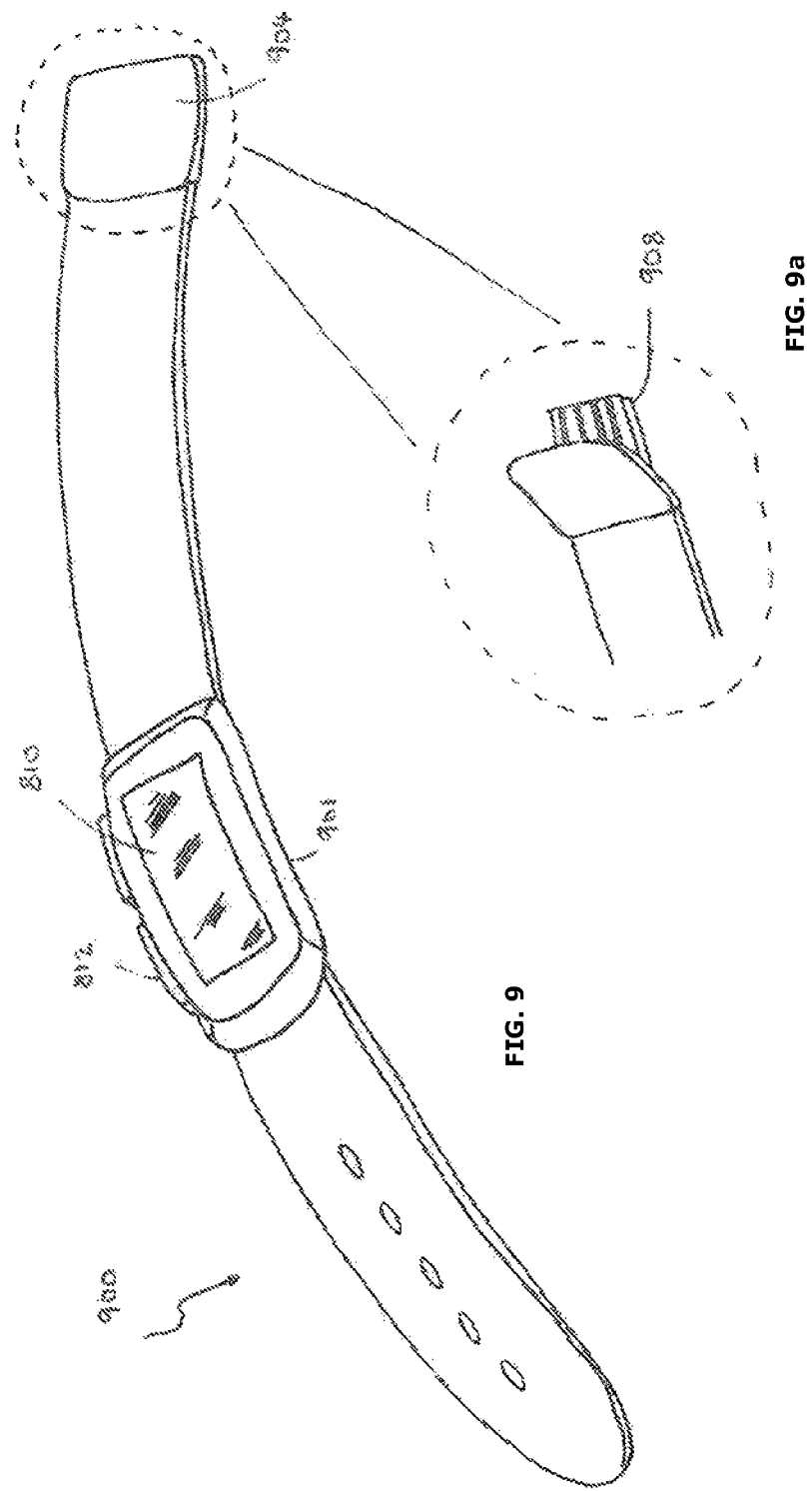

The device 800 includes a processor 802 connected to an input device 812 and a display screen 810, such as an LCD display. The input device 812 can include one or more buttons or switches (e.g. as shown in FIG. 9). The device 800 can further include an output device arranged to provide audible information to a user, such as alerts that a certain speed has been reached or a certain distance has been travelled.

FIG. 8 further illustrates an operative connection between the processor 802 and a GPS antenna/receiver 804. Although the antenna and receiver are combined schematically for illustration, the antenna and receiver may be separately located components. The antenna may be a GPS patch antenna or helical antenna for example.

The device 800 further includes an accelerometer 806, which can be a 3-axis accelerometer arranged to detect accelerations of the user in x, y and z directions. As will be explained in more detail below, the accelerometer may play a dual role: firstly as a means for determining a motion state of the wearer at a particular moment in time, and secondly as a pedometer for use when/if there is a loss of GPS reception. Although the accelerometer is shown to be located within the device, the accelerometer may also be a external sensor worn or carried by the user, and which transmits data to the device 800 via the transmitter/receiver 808.

The device may also receive data from other sensors, such as a footpad sensor 822 or a heart rate sensor 826. The footpad sensor may, for example, be a piezoelectric accelerometer that is located in or on the sole of the user's shoe. Each external sensor is provided with a transmitter and receiver, 824 and 828 respectively, which can be used to send or receiver data to the device 800 via the transmitter/receiver 808.

The processor 802 is operatively coupled to a memory 820. The memory resource 820 may comprise, for example, a volatile memory, such as a Random Access Memory (RAM), and/or a non-volatile memory, for example a digital memory, such as a flash memory. The memory resource 820 may be removable. As discussed in more detail below, the memory resource 820 is also operatively coupled to the GPS receiver 804, the accelerometer 806 and the transmitter/receiver 808 for storing data obtained from these sensors and devices.

Further, it will be understood by one of ordinary skill in the art that the electronic components shown in FIG. 8 are powered by a power source 818 in a conventional manner. The power source 818 may be a rechargeable battery.

The device 800 further includes an input/output (I/O) device 816, such as a USB connector. The I/O device 816 is operatively coupled to the processor, and also at least to the memory 820 and power supply 818. The I/O device 816 is used, for example, to: update firmware of processor 820, sensors, etc; transfer data stored on the memory 820 to an external computing resource, such as a personal computer or a remote server; and recharge the power supply 818 of the device 200. Data could, in other embodiments, also be sent or received by the device 200 over the air using any suitable mobile telecommunication means.

As will be understood by one of ordinary skill in the art, different configurations of the components shown in FIG. 8 are considered to be within the scope of the present application. For example, the components shown in FIG. 8 may be in communication with one another via wired and/or wireless connections and the like.

FIG. 9 illustrates a preferred embodiment of the device 800, wherein the device 800 is provided in the form of a watch 900. The watch 900 has a housing 901 in which is contained the various electronic components on the device as discussed above. Two buttons 812 are provided on the side of the housing 901 to allow the user to input data to the device, e.g. to navigation a menu structure shown on the display 210. Any number of buttons, or other types of input means, can alternatively be used as desired.

The watch 900 has a strap 902 for securing the device to a user's wrist. As can be seen the end of the strap 902 has a hinged cover 904 that can be lifted up, e.g. as shown in FIG. 9A, to reveal a USB connector 908. The connector can be inserted into any suitable USB port for power and/or data transfer as described above.

Figure 10:
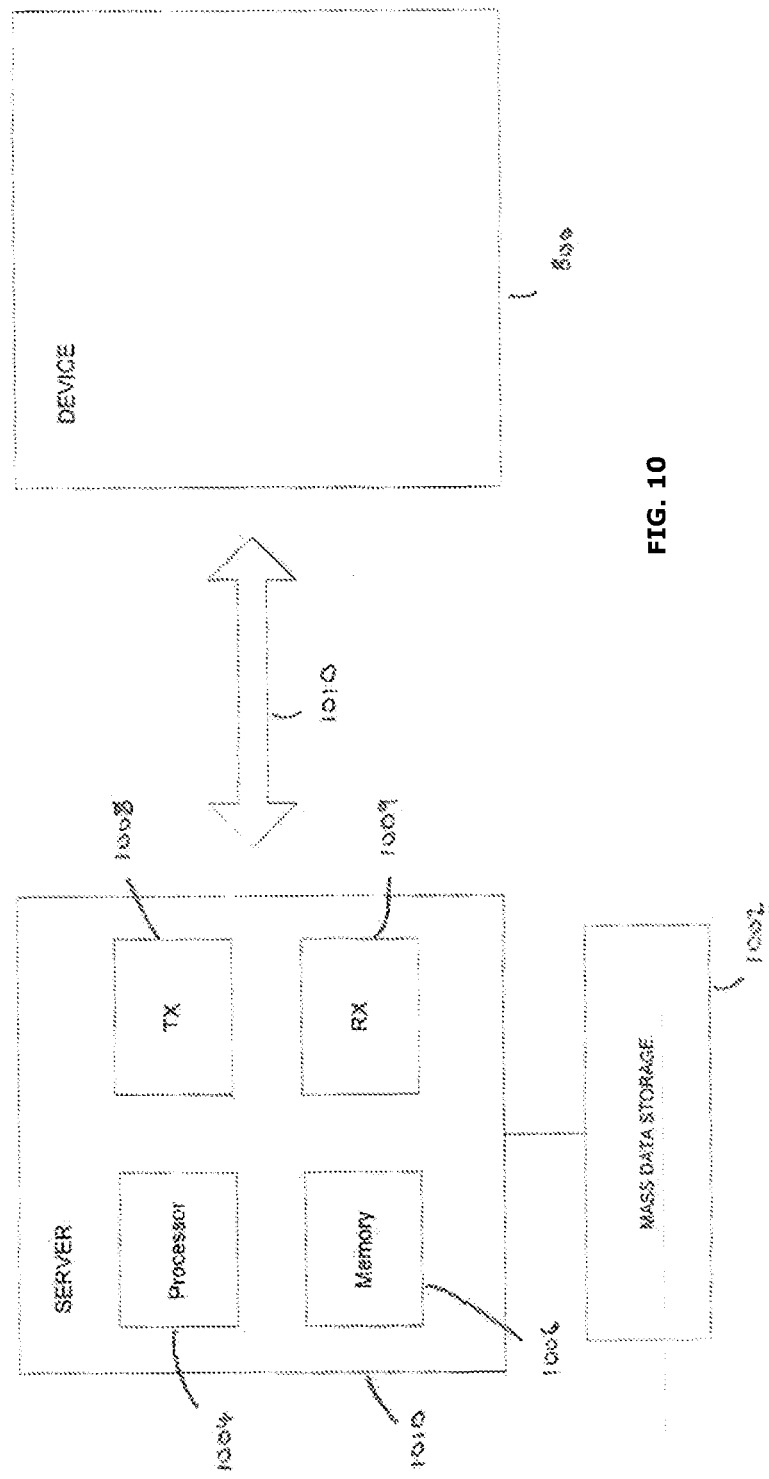
FIG. 10 is a schematic illustration of the manner in which a navigation device may receive information over a wireless communication channel.

In FIG. 10 the device 800 is depicted as being in communication with a server 1000 via a generic communications channel 1010 that can be implemented by any number of different arrangements. The server 1000 and device 800 can communicate when a connection is established between the server 1000 and the navigation device 800 (noting that such a connection can be a data connection via mobile device, a direct connection via personal computer via the internet, etc.).

The server 1000 includes, in addition to other components which may not be illustrated, a processor 1004 operatively connected to a memory 1006 and further operatively connected, via a wired or wireless connection, to a mass data storage device 1002. The processor 1004 is further operatively connected to transmitter 1008 and receiver 1009, to transmit and send information to and from device 800 via communications channel 1010. The signals sent and received may include data, communication, and/or other propagated signals. The functions of transmitter 1008 and receiver 1009 may be combined into a signal transceiver.

The communication channel 1010 is not limited to a particular communication technology. Additionally, the communication channel 1010 is not limited to a single communication technology; that is, the channel 1010 may include several communication links that use a variety of technology. For example, the communication channel 1010 can be adapted to provide a path for electrical, optical, and/or electromagnetic communications, etc. As such, the communication channel 1010 includes, but is not limited to, one or a combination of the following: electric circuits, electrical conductors such as wires and coaxial cables, fibre optic cables, converters, radio-frequency (RF) waves, the atmosphere, empty space, etc. Furthermore, the communication channel 1010 can include intermediate devices such as routers, repeaters, buffers, transmitters, and receivers, for example.

In one illustrative arrangement, the communication channel 1010 includes telephone and computer networks. Furthermore, the communication channel 1010 may be capable of accommodating wireless communication such as radio frequency, microwave frequency, infrared communication, etc. Additionally, the communication channel 1010 can accommodate satellite communication.

The server 1000 may be a remote server accessible by the device 800 via a wireless channel. The server 1000 may include a network server located on a local area network (LAN), wide area network (WAN), virtual private network (VPN), etc.

The server 1000 may include a personal computer such as a desktop or laptop computer, and the communication channel 1010 may be a cable connected between the personal computer and the device 800. Alternatively, a personal computer may be connected between the device 1000 and the server 1000 to establish an internet connection between the server 1000 and the device 800. Alternatively, a mobile telephone or other handheld device may establish a wireless connection to the internet, for connecting the device 800 to the server 1000 via the internet.

The server 1000 is further connected to (or includes) a mass storage device 1002. The mass storage device 1002 contains a store of at least digital map information. This digital map information can be used, together with data from the device, such as time-stamped location data obtained form the GPS receiver 804 and data indicative of motion of the wearer obtained from the accelerometer 806, footpad sensor 822, etc, to determine a route travelled by the wearer of the device 800, which can then be viewed by the wearer.

As will be appreciated, the device 800 is designed to be worn by a runner or other athlete as they undertake a run or other similar type of workout. The various sensors within the device 800, such as the GPS receiver 804 and the accelerometer 806, collect data associated with this run, such as the distance travelled, current speed, etc, and display this data to the wearer using the display screen 810.

Figure 2:
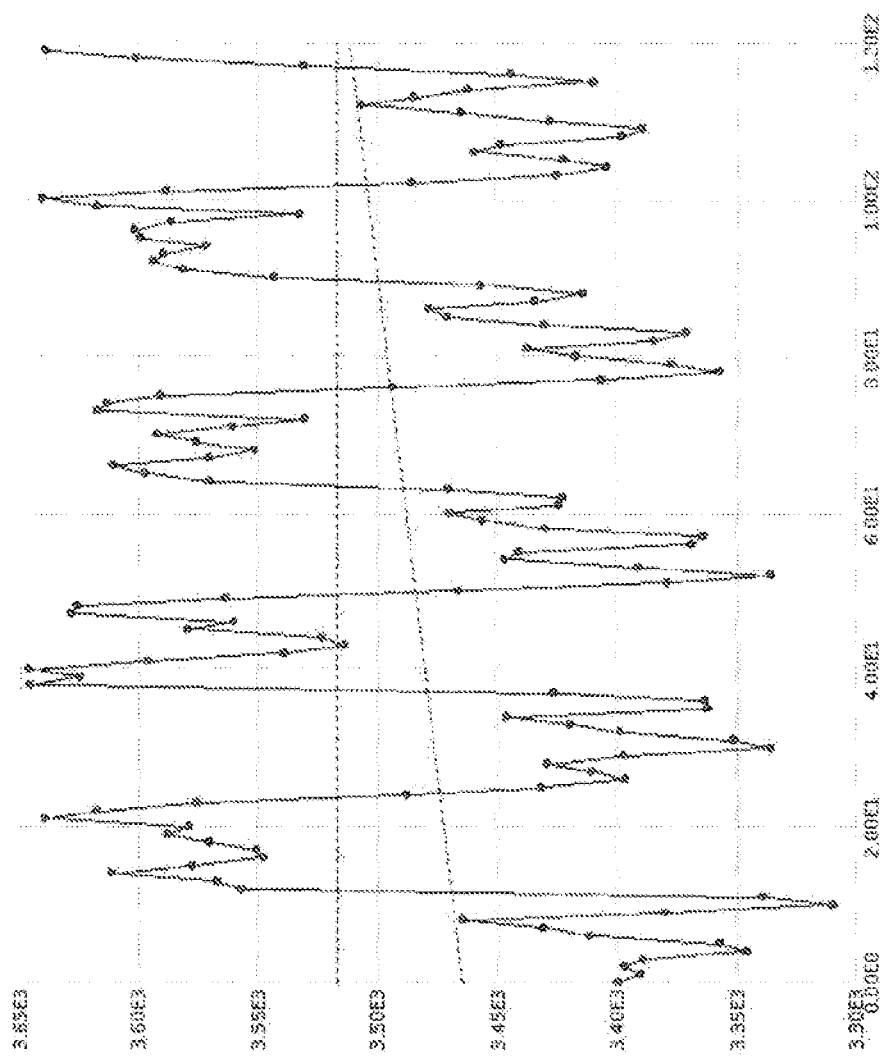
FIG. 2 illustrates raw acceleration data that is output from the accelerometer as a function of time.

FIG. 2 shows raw accelerometer data as a function of time that is output by a single-channel accelerometer mounted within the mobile device of FIG. 1. As noted above, in the mobile device of the described embodiment three accelerometers are used, each accelerometer being configured to measure acceleration in a direction orthogonal to that of the other accelerometers. Thus, three such acceleration channels are used, these are labelled x, y and z.

As is evident from FIG. 2, the acceleration varies as a function of time in response to the motion of the wearer of the watch. The skilled person will recognise that by using the value of this acceleration measured over time, measures of the wearer's time-dependent velocity, position and route can be derived.

The output from each of the three accelerometers is measured at time intervals of 0.1 seconds (i.e. 10 Hz). When measuring the accelerations generated by a person exercising, for example running, it is not generally necessary to measure the value of acceleration at rates higher that approximately 10 Hz. This is because the acceleration will not change dramatically over periods of less than 0.1 seconds. Accordingly, to avoid storage of unnecessary data the measurements are only taken at this maximum rate.

Nevertheless, over the course of for example one hour of exercising, a single channel of acceleration data still represents 36,000 points of data. As noted above, measurements of the acceleration in three mutually perpendicular axes are made to fully characterise the acceleration experienced by the mobile device. Thus, a total of 36,000*3=108,000 points of data will be stored for each hour of use. The method of the present invention permits a reduction in the amount of acceleration data stored whilst maintaining a dataset that is capable of generating approximations of the device's or wearer's speed and position as a function of time.

Figure 3:
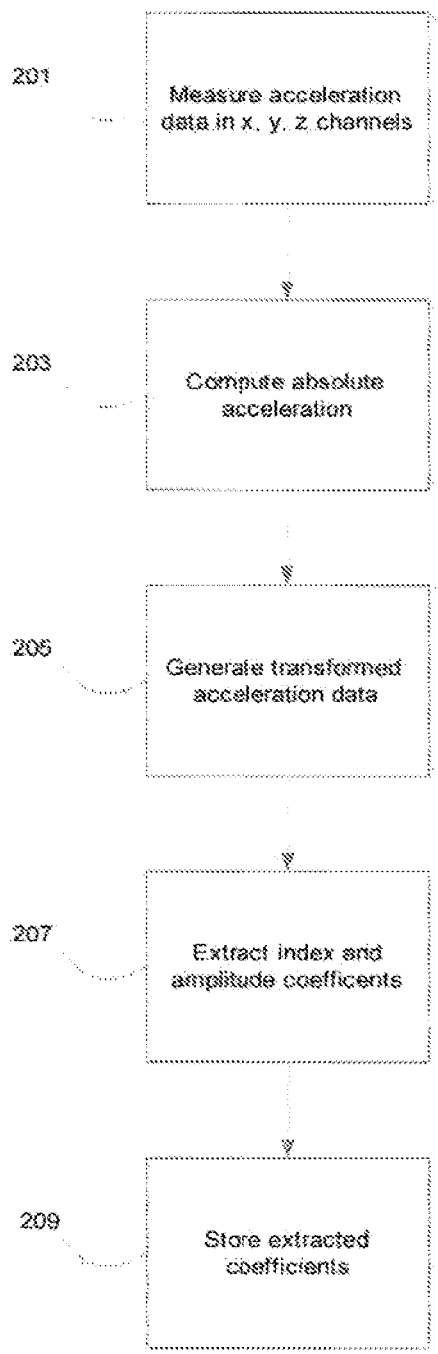
FIG. 3 illustrates the method of extracting, compressing and storing acceleration data.

FIG. 3 shows the general steps in the method of generating and storing transformed acceleration data. In step 201 the acceleration is measured in each of the x, y and z channels. Each measurement is repeated at time intervals of 0.1 seconds. In step 203 the absolute value of the acceleration is computed for each measurement made in step 201. In step 205 a Fast Fourier Transform (FFT) is applied to the absolute acceleration data generated in step 203. In step 207 selected frequency indices and associated coefficients are extracted from the FFT. In step 209 selected coefficients and indices are stored. Further details of each of these steps will now be explained with reference to FIGS. 4 to 7.

Figure 4:
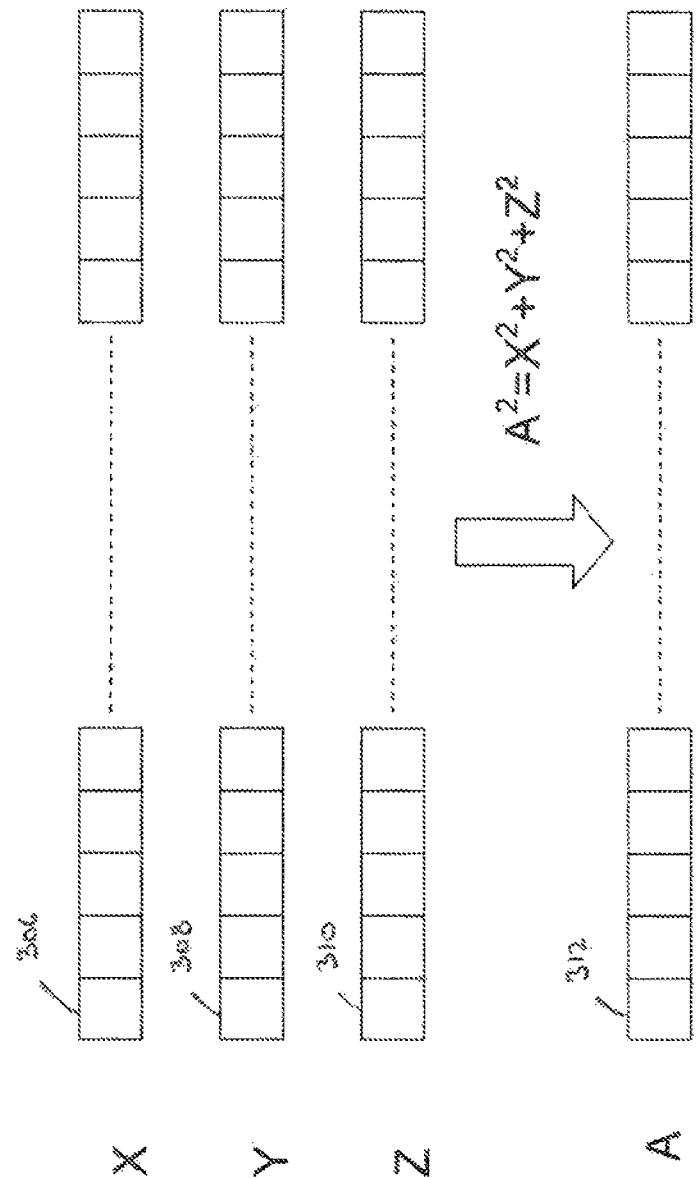
FIG. 4 illustrates the method of obtaining absolute values of the acceleration.

FIG. 4 illustrates details of the method of computing the absolute value of the acceleration (A) as a function of time (203). The inventors have noted that, in order to provide a measure of acceleration that can be used to determine the position and motion of the device, it is often not necessary to use a measure of the direction of the acceleration. Rather, it is normally sufficient to merely use a measure of the magnitude of the acceleration. Accordingly, the method of the present invention computes the total magnitude, or absolute value of the acceleration as measured from the three acceleration channels.

Each point from the x-channel (306) measured at a given time is combined with the corresponding points from the y-channel (308) and z-channel (310) to generate a single absolute acceleration value (312). The combination is effected by addition of the accelerations form the three channels in quadrature. Thus, the absolute acceleration (A) is given by:

$$A = \sqrt{X^2 + Y^2 + Z^2} \quad \text{Equation 1}$$

where X, Y and Z are the accelerations measured in the x, y and z channels respectively.

The absolute value of the acceleration (A) is used to generate approximate values of the time-dependent speed and position of the wearer of the device.

Figure 5A:
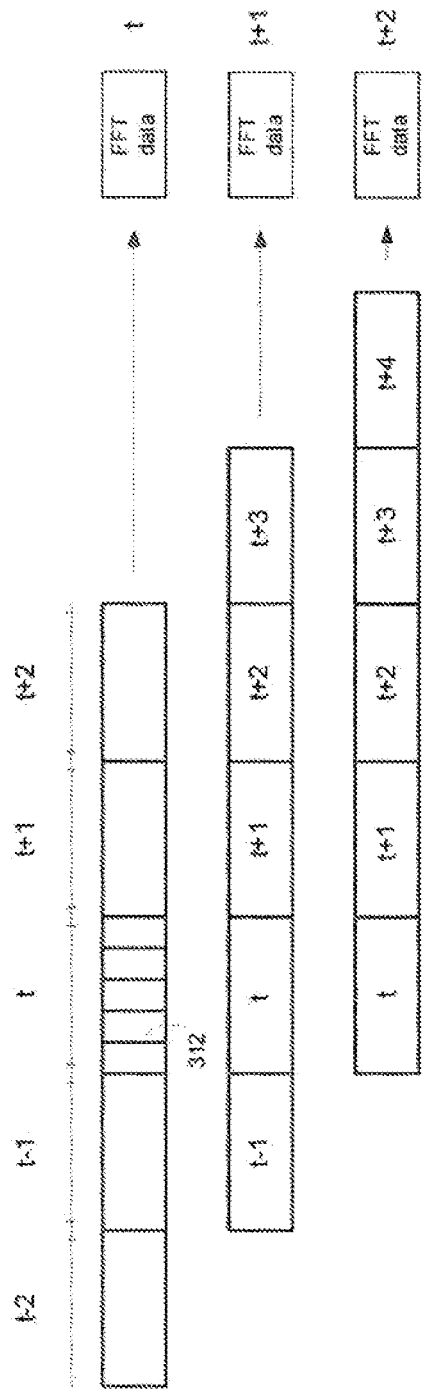
FIG. 5a illustrates the method of Fast Fourier transforming absolute acceleration data.

FIG. 5a illustrates details of the method of generating transformed acceleration data (205). The computed absolute acceleration values (312) comprise a series of data points, which represent the absolute acceleration determined at intervals of 0.1 s. An FFT is repeatedly applied to the series of data points at a rate of 1 Hz. On each application of the FFT, a data window of 5 seconds is used which, for a measurement rate of 10 Hz, corresponds to a series of 50 consecutive data points. The window of 5 seconds is constructed from a current second, and periods of 2 seconds either side of the current second. In other words, if t is the current second, t−1 is the preceding second, t+1 is the following second and so on, then the window will correspond to seconds: (t−2), (t−1), t, (t+1) and (t+2). Since the FFT is applied at a rate of 1 Hz, the subsequent application of the FFT is made on the window comprising the data from (t−1), t, (t+1), (t+2) and (t+3) seconds.

By applying the FFT in this manner the method permits FFT data to be collected at a rate of 1 Hz even though the effective measurement rate of the acceleration data is 10 Hz. Thus, a reduction in the amount of data that need be stored is achieved.

Those skilled in the art will recognise that applying an FFT to a series of time-domain data points will generate an output that describes the data in the frequency domain. The data output from the FFT is in the form of indices describing frequencies, together with associated coefficients that describe the amplitude associated with each of the frequencies. The time-domain data can, if desired, be reconstructed from these indices and coefficients by application if an inverse Fourier Transform.

Figure 5B:
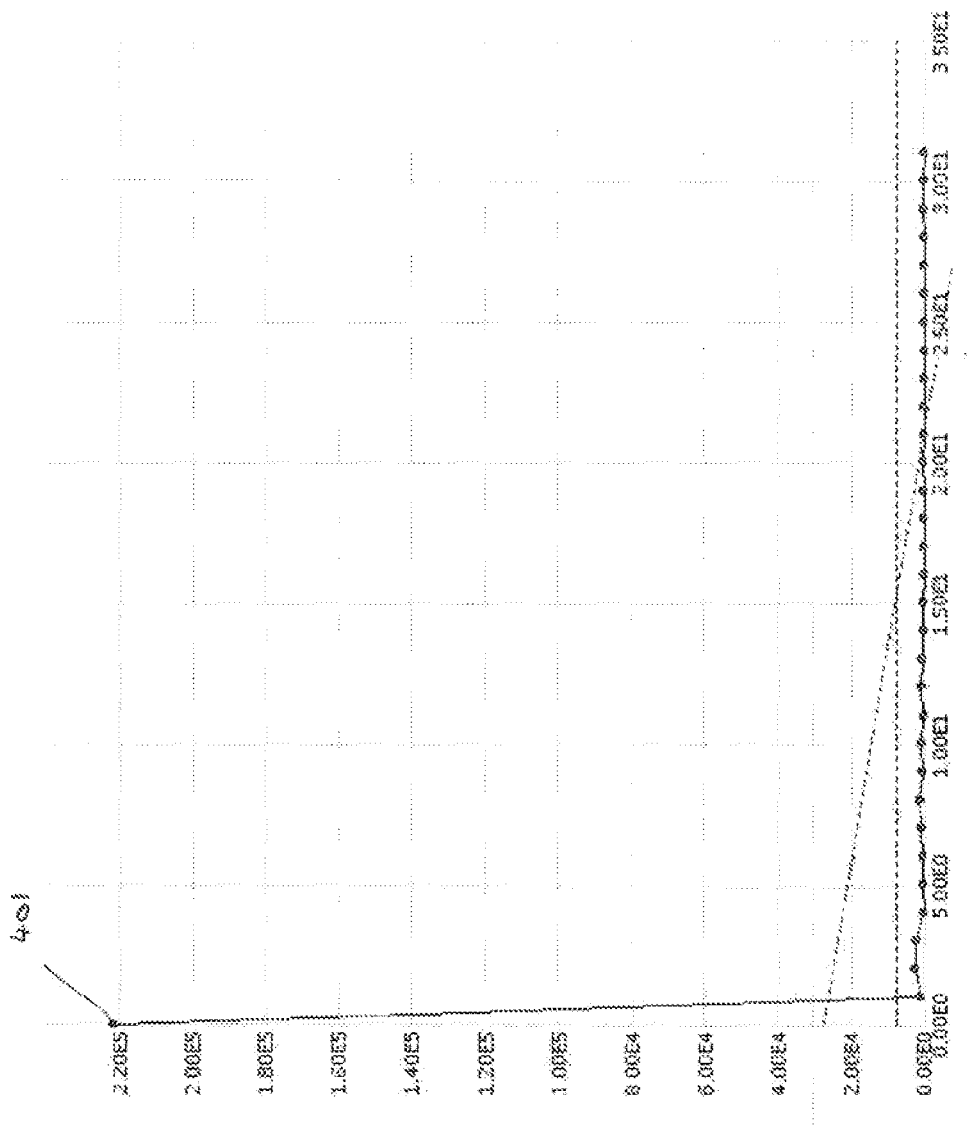
Figure 5C:
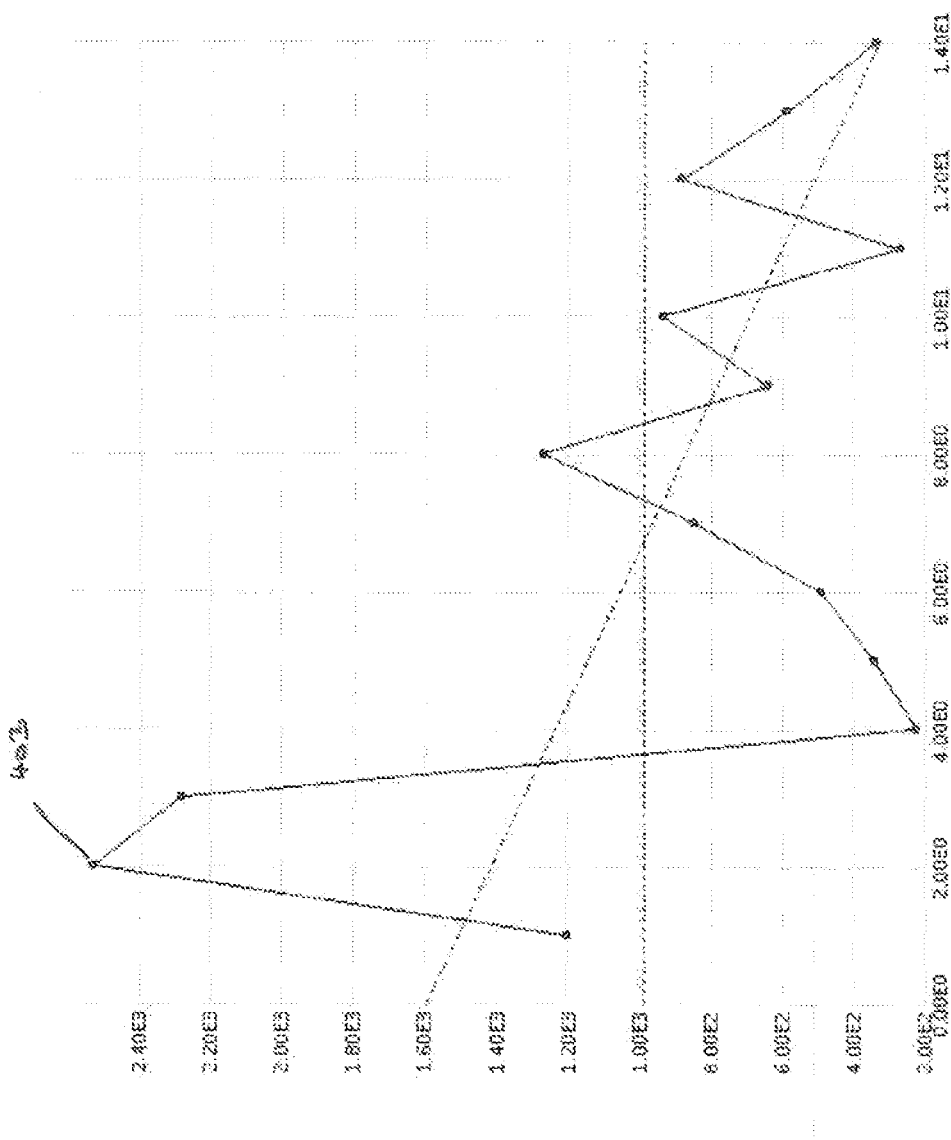
FIG. 5c illustrates detail of the output shown in FIG. 5b.

FIG. 5b illustrates the result of applying an FFT as described above. As can be seen from the figure, by far the largest component of the FFT output is the DC value (401), in other words the coefficient at a frequency of 0 Hz. FIG. 5c illustrates the same FFT output as FIG. 5b, however in FIG. 5c the dominant DC component (401) has been removed to better illustrate the remaining data. The remaining data comprises a series of peaks and troughs representing coefficients for frequencies other than 0 Hz. In the sample data of FIG. 5c, the amplitude of the data exhibits a general decrease with increasing frequency. Aside from the DC component (401), the next largest peak (403) has an amplitude that is approximately 1% that of the DC amplitude, while the subsequent peaks have even smaller amplitudes.

The inventors have noted that it is not necessary to store all indices and coefficients from the FFT in order to provide sufficient data to generate approximations for the speed and position of the device. Rather, it is sufficient to store four values; the DC value (401) (i.e. the coefficient for zero frequency); the index describing the frequency at which the first maximum (403) excluding the DC value occurs; the amplitude associated with this first maximum (403); and the sum of all amplitude values excluding the DC amplitude (401).

FIGS. 6a and 6b show details of the file structure used to store the selected output data from the FFT. The file structure comprises two blocks; the file header, and the data block. With reference to FIG. 6a the file header (501) comprises a series of different data fields. The first field is the file version field (503). This contains 2 bytes of data that indicate the version of the acceleration data file to which the rest of the file relates. The second and third fields are the header size (505) and block header size (507) fields respectively. These each contain two bytes of data detailing the size of the file header, and their purpose is to allow forward and backward compatibility for different versions of acceleration data files. The fourth field is the device firmware field (509), which contains two bytes of data used to indicate the firmware version of the mobile device. The final field in the file header is the accelerometer firmware field (511). This field contains two bytes of data that indicate the firmware version used by the acceleration device, if a separate acceleration device is used.

With reference to FIG. 6b, the data block (513) of the file structure contains the selected acceleration data The data block (513) contains four data fields, each of 1 byte of data. In the first field of the data block (515), the DC value of the FFT is stored. In the second field (517) the index value of the first maximal amplitude is stored. In the third field (519) the maximum value of the amplitude for the index value stored in the second field (517) is stored. While in the fourth field, the sum of all of the amplitudes excluding the DC component is stored.

Figure 7:
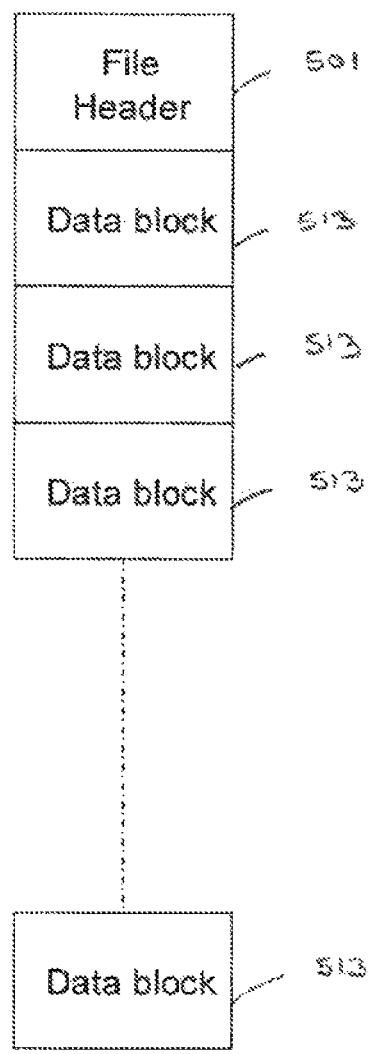
FIG. 7 illustrates an example of a complete file in the format of the invention.

FIG. 7 illustrates the complete file format. In general, the file structure comprises many data blocks (513) appended to a single header (501). Thus, by implementing the method as described above, the file size necessary to record acceleration data for one second is four bytes plus the header (501) size of 10 bytes. To record data for one hour, the data block (513) size will be 4*60*60=1440 bytes plus 10 bytes for the single header (501).

In an alternative embodiment, a different set of coefficients from the FFT is stored. In the alternative embodiment, the frequency index of the first maximum is stored, as is its associated amplitude coefficient. In addition, the frequency index of the second maximum and its associated amplitude value are also stored.

It will be appreciated that whilst various aspects and embodiments of the present invention have heretofore been described, the scope of the present invention is not limited to the particular arrangements set out herein and instead extends to encompass all arrangements, and modifications and alterations thereto, which fall within the scope of the appended claims.

For example, whilst embodiments described in the foregoing detailed description refer to GPS, it should be noted that the navigation device may utilise any kind of position sensing technology as an alternative to (or indeed in addition to) GPS. For example, the navigation device may utilise other global navigation satellite systems, such as the European Galileo system. Equally, it is not limited to satellite-based systems, but could readily function using ground-based beacons or other kind of system that enables the device to determine its geographic location.

It will also be well understood by persons of ordinary skill in the art that whilst the preferred embodiment may implement certain functionality by means of software, that functionality could equally be implemented solely in hardware (for example by means of one or more SICs (application specific integrated circuit)) or indeed by a mix of hardware and software.

Lastly, it should be noted that whilst the accompanying claims set out particular combinations of features described herein, the scope of the present invention is not limited to the particular combinations hereafter claimed, but instead extends to encompass any combination of features or embodiments herein disclosed irrespective of whether or not that particular combination has been specially enumerated in the accompanying claims at this time.

The invention claimed is:

1. A method comprising the steps of:
   receiving, by a processor, a location of a mobile device configured to be transported, carried or worn by a user determined at a plurality of times during a journey from a first location to a second location;
   receiving, by the processor, acceleration values indicative of the movement of the user and/or device a plurality of times during the journey measured at a first frequency;
   generating, by the processor, values representative of the measured acceleration values at a second frequency, which is lower than the first frequency, said step of generating comprising:
   defining a plurality of time windows, each time window containing a plurality of measured acceleration values; and
   applying a transformation to the measured acceleration values within each time window to generate a plurality of transformed values; and,
   selecting, for each time window, at least one of said plurality of transformed values and/or one or more parameters derived from the plurality of transformed values to be stored;
   storing: (i) the received locations and/or data derived therefrom; and (ii) the selected data derived from the acceleration values; and
   transmitting the stored data from the mobile device to a remote server for use in providing a representation of the journey.

2. The method as claimed in claim 1, wherein the acceleration values are measured using one or more accelerometers.

3. The method as claimed in claim 1, wherein the first frequency is between 1 Hz and 20 Hz.

4. The method as claimed in claim 1, wherein the acceleration values are stored in a data buffer.

5. The method as claimed in claim 1, further comprising determining an absolute acceleration value indicative of the movement of the user from the measured acceleration values.

6. The method as claimed in claim 1, wherein the plurality of time windows are defined such that a portion of one time window overlaps a portion of an adjacent time window.

7. The method as claimed in claim 1, wherein the second frequency is between 0.1 and 2 Hz.

8. The method as claimed in claim 1, wherein transformation applied to the measured acceleration values comprises a fast Fourier transformation.

9. The method as claimed in claim 1, further comprising:
   applying a transformation to the acceleration values within each time window to generate a frequency spectrum; and
   storing one or more parameters associated with the frequency spectrum.

10. The method as claimed in claim 9, wherein the one or more parameters associated with the frequency spectrum comprise at least one of: one or more indexed coefficients; and one or more parameters derived from the indexed coefficients.

11. The method as claimed in claim 10, wherein said one or more parameters are selected from the group consisting of: (i) the zero index amplitude; (ii) the largest nonzero index amplitude; (iii) the index associated with the largest amplitude; and (iv) the sum of all the non-zero index amplitudes.

12. A mobile device configured to be transported, carried or worn by a user, comprising:
   a receiver for determining the location of the mobile device at a plurality of times during a journey from a first location to a second location;
   one or more accelerometers for measuring acceleration values indicative of the movement of the user and/or device at a plurality of times during the journey at a first frequency;
   at least one processor arranged to generate values representative of the measured acceleration values at a second frequency, which is lower than the first frequency, by:

defining a plurality of time windows, each time window containing a plurality of measured acceleration values; and applying a transformation to the measured acceleration values within each time window to generate a plurality of transformed values; and the at least one processor being further arranged to select for each time window, at least one of said plurality of transformed values and/or one or more parameters derived from the plurality of transformed values to be stored;

at least one data storage device for storing data received from and/or derived from the receiver and the selected data derived from the one or more accelerometers; and a transmitter for transmitting the stored data from the mobile device to a remote server for use in providing a representation of the journey.

13. The mobile device as claimed in claim 12, wherein said one or more accelerometers comprise a three-axis accelerometer.

14. The mobile device as claimed in claim 12, wherein the receiver comprises a global navigation satellite system (GNSS) receiver for determining the location of the user.

15. The mobile device as claimed in claim 12, wherein the mobile device is a portable personal training device comprising a housing having a strap for securing the device to a user.

16. A non-transitory computer-readable medium storing a set of instructions which, when executed by at least one processor, causes the at least one processor to perform a method, the method executed by the set of instructions comprising:

receiving a location of a mobile device configured to be transported, carried or worn by a user determined at a plurality of times during a journey from a first location to a second location;

receiving acceleration values indicative of the movement of the user and/or device a plurality of times during the journey measured at a first frequency;

generating values representative of the measured acceleration values at a second frequency, which is lower than the first frequency, said step of generating comprising:

defining a plurality of time windows, each time window containing a plurality of measured acceleration values; and applying a transformation to the measured acceleration values within each time window to generate a plurality of transformed values; and, selecting, for each time window, at least one of said plurality of transformed values and/or one or more parameters derived from the plurality of transformed values to be stored;

storing: (i) the received locations and/or data derived therefrom; and (ii) the selected data derived from the acceleration values; and transmitting the stored data from the mobile device to a remote server for use in providing a representation of the journey.

17. The computer-readable medium as claimed in claim 16, further comprising determining an absolute acceleration value indicative of the movement of the user from the measured acceleration values.

18. The computer-readable medium as claimed in claim 16, further comprising:

applying a transformation to the acceleration values within each time window to generate a frequency spectrum; and storing one or more parameters associated with the frequency spectrum.

19. The computer-readable medium of claim 18, wherein the one or more parameters associated with the frequency spectrum comprise at least one of: one or more indexed coefficients; and one or more parameters derived from the indexed coefficients.

20. The computer-readable medium of claim 19, wherein said one or more parameters are selected from the group consisting of: (i) the zero index amplitude; (ii) the largest nonzero index amplitude; (iii) the index associated with the largest amplitude; and (iv) the sum of all the non-zero index amplitudes.

* * * * *